United States Patent [19]
Böbel et al.

[11] Patent Number: 5,387,309
[45] Date of Patent: Feb. 7, 1995

[54] PROCESS FOR THE MEASUREMENT OF THE THICKNESS AND REFRACTIVE INDEX OF A THIN FILM ON A SUBSTRATE, AND AN APPARATUS FOR CARRYING OUT THE PROCESS

[75] Inventors: Friedrich Böbel, Uttenreuth; Norbert Bauer, Erlangen, both of Germany

[73] Assignee: Fraunhofer Gesellschaft zur Förderung der angewandten Forschung e.v., Munich, Germany

[21] Appl. No.: 952,834

[22] PCT Filed: May 29, 1991

[86] PCT No.: PCT/DE91/00461
§ 371 Date: Nov. 30, 1992
§ 102(e) Date: Nov. 30, 1992

[87] PCT Pub. No.: WO91/19025
PCT Pub. Date: Dec. 12, 1991

[30] Foreign Application Priority Data
May 30, 1990 [DE] Germany .............. 4017440

[51] Int. Cl.[6] ............................ C30B 25/16
[52] U.S. Cl. ...................... 117/85; 437/250;
427/8; 427/9; 427/10; 204/192.33; 204/298.03;
117/86; 118/712; 118/688

[58] Field of Search .............. 204/192.33, 298.03;
427/10, 9, 8; 156/601; 437/250

[56] References Cited
U.S. PATENT DOCUMENTS
3,620,814 11/1971 Clark et al. .................. 427/10
5,091,320 2/1992 Aspnes et al. ................ 156/601
5,096,533 3/1992 Igarashi ...................... 156/601

Primary Examiner—Robert Kunemund
Assistant Examiner—Ramamohan Rao Paladugu
Attorney, Agent, or Firm—Antonelli, Terry, Stout & Kraus

[57] ABSTRACT

A process and apparatus for in situ measurement of the thickness of a thin film on a substrate using interference effects in the thin film. Thermal radiation of the substrate is utilized as a source of interfering bundles of electromagnetic radiation which intensity thereof is measured with a charge-coupled-device camera, and signal-processing electronics is utilized for determining in accordance with the Airy formula the thickness of the thin film on the substrate in the planar direction of the thin film and the index of refraction thereof. The low time constant for the measurement and evaluation enables the process for the recording of measurements be used for the control of coating or removal procedures.

21 Claims, 2 Drawing Sheets

PROCESS FOR THE MEASUREMENT OF THE THICKNESS AND REFRACTIVE INDEX OF A THIN FILM ON A SUBSTRATE, AND AN APPARATUS FOR CARRYING OUT THE PROCESS

FIELD OF THE ART

The invention relates to a process for the spatially resolved measurement of the thickness of a thin film on a substrate, as well as to a device for performing the process.

Film thickness measurements are counted among the most significant auxiliary means in quality control during semiconductor manufacture, especially for checking individual process steps. Since the process environment, for example within a semiconductor-producing equipment, can vary greatly in spatial respects, it is particularly desirable to measure the film thickness over the entire wafer surface.

With increasing integration of components, the costs per wafer have risen considerably; for this reason, a complete check of each individual process step is the objective in order to recognize flawed parts as early as possible and to be able to sort these out.

STATE OF THE ART

A process for measuring the growth rate of an epitaxial layer on a substrate has been known from the technical publication by A. J. Spring Thorpe et al., "In Situ Growth Rate Measurements During Molecular Beam Epitaxie [sic!] Using an Optical Pyrometer", Applied Physics Letter, 55: 2138–2140 (1989).

This article describes measurement of the surface temperature of the substrate by means of an optical pyrometer during application of the layer. During this step, oscillations occur in the temperature which can be associated with the growth rate of the layer. However, it is not possible to measure, with this process, the absolute value of the layer thickness; furthermore, no spatial resolution over the area of the layer is possible.

One possibility of determining the thickness of layers resides in the interference of light beams reflected on the two surfaces of the layer. In an arrangement as disclosed, for example, in F. Kohlrausch, "Praktische Physik" [Practical Physics], vol. 1, 23rd edition, 1984, page 667, the phase difference of interfering beams is determined by their angle of inclination. Since all bundles of rays with the same angle of inclination are imaged independently of their point of origin during interference in the same image point, a locally resolved measurement of the layer thickness is not possible.

Moreover, the known interferometric methods for layer thickness determination are not directly suitable for measurement during production of the layer on account of the time required for the measurement and the necessary manipulating mechanisms.

Furthermore, a process for measuring the film thickness during application of the film has been known from DE 19 39 667 A1. In this process, the film thickness is determined by detecting the electromagnetic radiation emitted by the film.

Also, a process and apparatus for determining the layer thickness and the index of refraction of thin, transparent layers has been known from DE 24 48 294 A1.

DISCLOSURE OF THE INVENTION

The invention is based on the object of indicating a process permitting, during application of a film on a substrate, a spatially resolved measurement of the thickness of the film over the entire surface.

Furthermore, a device for carrying out this process is to be made available.

This object has been attained, according to the invention, by measuring and evaluating the intensity of two or more interfering electromagnetic bundles of rays which exhibit a phase difference after passing through differing path lengths in the film, and by providing that the thermal radiation of the substrate serves as the source of the electromagnetic radiation, and that all frequency proportions are filtered out of the continuous spectrum of the thermal radiation except for an approximately monochromatic proportion.

A bundle of rays emanating due to the thermal radiation from any desired point in the substrate is refracted on the interface between the substrate and the film and, after passing through the film, is separated on the vacant surface of the latter by partial reflection into a reflected and a transmitted component beam. The reflected beam, after reflection on the interface, is again separated by partial reflection into a reflected component beam and a second transmitted component beam. Since the two transmitted component beams emanate from the same source, they are superimposed in coherent fashion and interfere after imaging with an imaging optic customary in interferometry in an image point. The intensity measured in the image point is a function of the phase difference between the two transmitted component beams and thus a function of the thickness of a limited area of the film adjacent to the joint source of the component beams. With interference of more than two component beams, the result does not change in its quality.

On account of the plurality of sources of electromagnetic radiation in the substrate, the spatial distribution of the thickness of the film can be measured over the entire area of the film.

In order to prevent the interferences from being averaged out at varying wavelengths of the thermal radiation, all frequency proportions except for an approximately monochromatic proportion are filtered out of the continuous spectrum.

According to features of the present invention, the component bundles emanating from the film are conducted through a narrowband filter and imaged by an imaging optic, in the simplest case by a lens, on a locally resolving detector. The output signals of the detector, corresponding to the intensities of the interfering component beams, are fed to a signal-processing electronic circuit in order to determine, with the aid of Airy's formula, the film thicknesses and indices of refraction of the film. A multidimensional image of the film thickness and refractive index distribution can be built up in the layer by means of the evaluated signal.

In order to avoid the necessity of using appliances of high sensitivity (e.g. residual light amplifiers) when selecting a detector, the substrate is heated. Thereby, the intensity of the thermal radiation is enhanced.

According to features of the present invention, line or matrix detectors can be utilized as the local-resolution or position-sensitive detectors. Thus, the distributions of the film thicknesses and refractive indices can be measured either over the entire film or along a line-shaped area. In the last-mentioned process, the expenditure in apparatus is minimized while foregoing complete information.

In the process according to this invention, the component bundles interfering in an image point yield information averaged over a limited region of the film. This region is the smaller, the lower the influence of the multiple interferences and the smaller the angle between the surface normal of the layer and the exiting component beams. A high spatial resolution in the plane of the film surface is achieved by means of the process wherein the component beams exit approximately perpendicularly from the surface of the film.

An especially advantages further development of the process provides a time-dependent measurement. On account of the time-dependent measurement, every change in film thickness is directly monitored. Based on the low time constants of the measurement and evaluation of the signals, the process of this invention is suitable for measured value recording for process control operations. This can involve application procedures wherein a layer is applied to a substrate by means of chemical and/or physical reactions. Examples of such methods are chemical vapor deposition (CVD), plasma enhanced chemical vapor deposition (PECVD), molecular beam epitaxy (MBE), or electron beam vapor deposition.

If an already applied film is to be removed, then it is also possible by means of the process of this invention to measure the film thickness during a removal process, e.g. dry etching.

The device for performing the process consists of a substrate holder to accommodate the substrate, a narrow-band filter filtering out an approximately monochromatic radiation from the continuous spectrum of the thermal radiation of the substrate, an imaging optic, and a local-resolution or position-sensitive detector. All of these components are arranged along an optical axis. The outputs of the local-resolution detector are connected to a signal-processing electronic circuit.

According to a feature of the present invention, the substrate holder is arranged in a process chamber in order to be able to measure the thickness of a film application to a substrate in the process chamber. In accordance with the process, the chamber exhibits inlet valves for the process gas. For coupling out of the radiation, a vacuum-tight window is set into a wall of the process chamber. All other components required for performing the process are mounted externally of the process chamber.

In accordance with other features of the present invention, cameras with semiconductor image converters are advantageously utilized as detectors. Suitable CCD cameras (charge coupled device) having a high spatial resolution power and adequate sensitivity are also known within the wavelength range of thermal radiation.

When using a camera having semiconductor image converters arranged in line pattern, a grating monochromator or a prism monochromator can be employed.

When utilizing a camera having semiconductor image converters arranged in matrix fashion, a narrowband interference filter is utilized for rendering the thermal radiation monochromatic.

The wavelength $\lambda_o$ of the maximum transmission of the filter is fixed so that the substrate is opaque to this wavelength, but the film is transparent thereto. With a film of silicon dioxide on a silicon substrate, the wavelength of the maximal transmission $\lambda_o = 1$ $\mu m$ represents a suitable choice. The half transmission width $\Delta$ of the filter is chosen so that $\lambda_o/\Delta \geq 100$. This ensures that the interference phenomena pertaining to varying wavelengths will not interact in disturbing fashion.

In order to attain a higher intensity of the electromagnetic radiation, the substrate is heated up. Heating is accomplished, for example, by means of a heating element mounted in the substrate holder. This arrangement is resorted to in case the growth of the film thickness during MBE processes is to be observed since such a heater has already been included in the associated process chamber.

For heating the substrate, it is also possible, for relatively large regions of the process chamber to serve as a furnace, as is customary in silicon oxidation processes.

The advantages attained by this invention reside particularly in that the layer thicknesses of a film can be measured in spatially resolved fashion over the entire surface of the film. It is thus safely possible to determine local deviations from given desired values. Based on the results of the measurement, the device can be optimized for carrying out a deposition process or a removal process.

The process permits rapid recording and evaluation of measured values so that the growth procedure of a film on a substrate can be observed as a function of time. Due to the small time constant of the measurement, the process can also be utilized for process control.

The process is distinguished by high resolution in the growth direction as well as in the plane of the film. The process is insensitive to high ambient temperatures and with respect to chemically reactive gases and plasmas so that it is suited for the control of many deposition and/or removal operations. In contrast to conventional interferometric processes, the method of this invention is also insensitive to mechanical disturbances, such as, for example, vibrations.

Since no external light source is required, the process is particularly well suited for use in high vacuum (HV) and ultrahigh vacuum (UHV) processes. A window is enough for coupling out the thermal radiation. The process requires only a small number of components and therefore has a favorable cost/utility ratio.

Areas of usage are preferably the in situ measurement of two-dimensional film thickness distributions in layers applied to a substrate in oxidizing furnaces, sputtering, deposition, CVD or MBE facilities. It is likewise suitable for determining the concomitant variables, such as growth rate, reflection and absorption coefficients.

Since the process according to this invention has not as yet been described in the literature it is proposed to introduce therefor the term "pyrometric interferometry".

BRIEF DESCRIPTION OF THE DRAWINGS

One embodiment of the invention is illustrated in the drawings and will be described in greater detail below. In the drawings.

DESCRIPTION OF EMBODIMENTS

Figure 1:
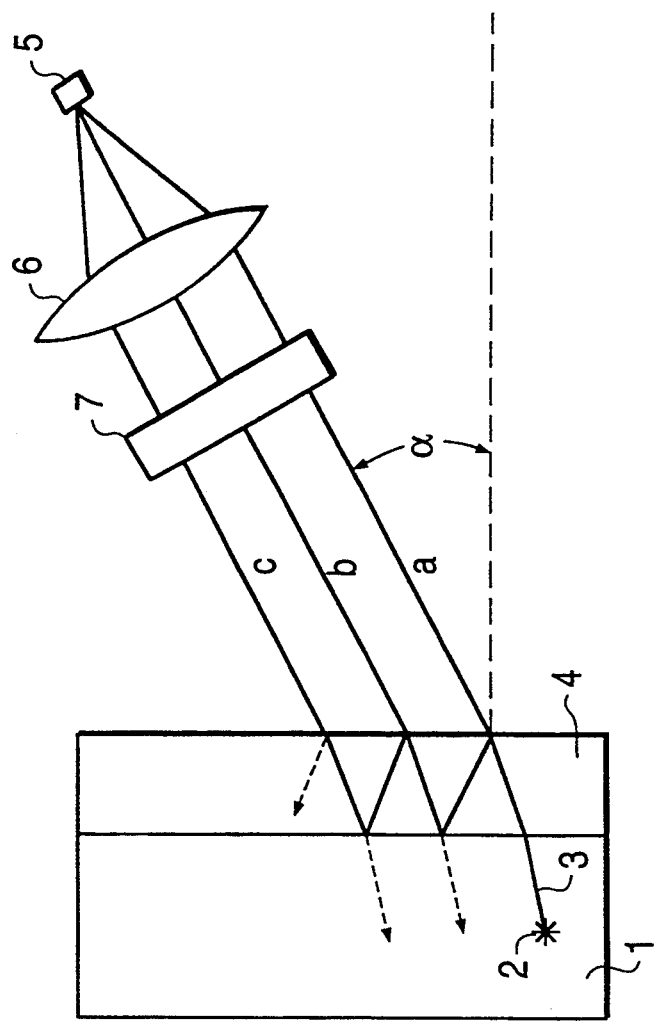
FIG. 1 shows a schematic view of the measuring principle of the process according to the invention.

An arbitrary point in a substrate 1 of FIG. 1 acts as the source 2 of thermal radiation and transmits the bundle of rays 3 that is refracted and, respectively, reflected on the interface between the substrate 1 and a film 4 applied to the substrate, as well as on the vacant surface of the film 4. Since the thus-produced component beams a, b, c emanate from the same source 2, they are superimposed in coherent fashion and interfere with one another in a point of the detector 5. The mutual spacing of the component beams a, b, c and thus the area of the film 4 covered by the component beam 3 is the smaller, the smaller the angle α between the surface normal and the component beams a, b, c. In order to achieve a maximally high spatial resolution power, the angle α is chosen to be approximately zero.

The imaging of the component beams a, b, c on the detector 5 is effected by the imaging optic 6, consisting in the illustrated case of a collector lens. To eliminate a mutual influencing of the interferences of various wavelengths of the thermal radiation, the radiation is passed through a narrowband filter 7.

The component beams emanating from various sources in the substrate are superimposed on each other in various points of the detector 5 whereby a spatially resolved image of the intensities of the interfering radiation emanating from various regions of the film 4 is produced.

Figure 2:
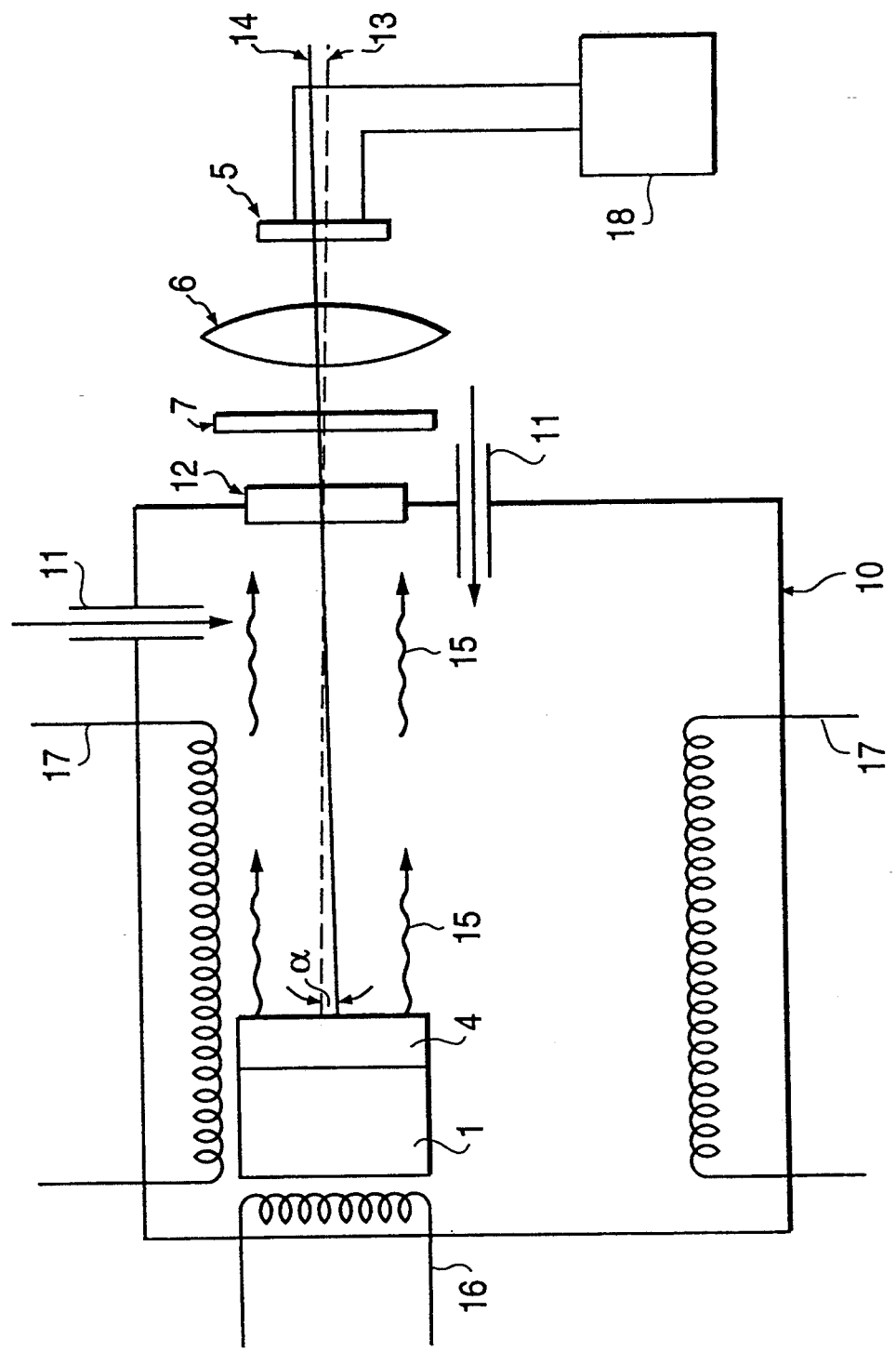
FIG. 2 shows a schematic view of a device according to the invention.

FIG. 2 shows schematically a device in accordance with this invention. The substrate 1 with the film 4 is located in a process chamber 10. The structure of the process chamber 10 is adapted to the process with the aid of which the film 4 is applied to or removed from the substrate 1. The process chamber 10 is designed, for example, as a vacuum chamber exhibiting inlet valves 11 to afford entrance of process gases. A window 12 for coupling out the heat radiation 15 of the substrate 1 is installed in vacuum-tight fashion in the wall of the process chamber 10. In order to raise the intensity of thermal radiation, the substrate 1 can be heated with the aid of the heating element 16. In addition, or as an alternative, heating elements 17 can be arranged in the process chamber 1 so that the chamber acts like a furnace.

Along the optical axis 13, the filter 7, the imaging optic 6 and the detector 5 are disposed outside of the process chamber 10. The angle α between the optical axis 13 and the surface normal 14 of the film 4 is approximately zero.

The window 12 must be transparent in the transmission range of the filter 7. Suitable materials are chemically resistant materials which are of low water solubility or water-insoluble and exhibit good transmission properties in the wavelength range of near and middle-range infrared radiation (0.7 μm to 1.2 μm). Suitable materials are, for example, $SiO_2$, $Al_2O_3$, ZnSe, CdTe, ZnS, $LaF_3$.

The imaging optic 6 images the surface of the film 4 on the detector 5. The same conditions apply for the transmission properties of the imaging optic as valid for the window 12. The electrical signal outputs of the detector 5 are connected to a signal-processing electronic circuit 18.

We claim:

1. A process for enabling spatially resolved measurement of a thickness of a thin film on a substrate, comprising the steps of utilizing thermal radiation of the substrate as a source of electromagnetic radiation, causing at least two bundles of electromagnetic radiation exhibiting a phase difference after passing through differing path lengths in the thin film to emanate from thin film at different points in a planar direction of the thin film, filtering from the at least two bundles of electromagnetic radiation all frequency proportions other than an approximately monochromatic proportion out of a continuous spectrum of the thermal radiation, interfering the at least two filtered bundles of electromagnetic radiation, measuring the intensities of the interfering bundles of electromagnetic radiation, and evaluating the measured intensities so as to at least obtain the spatially resolved measurement of the thickness of the thin film on the substrate in the planar direction of the thin film.

2. A processing according to claim 1, wherein the step of evaluating includes obtaining the refractive index of the thin film.

3. A process according to claim 2, wherein the thermal radiation emanates from an arbitrary point in the substrate, and the step of causing includes refracting the thermal radiation on an interface between the substrate and the thin film having the thickness thereof to be measured and separating the refracted thermal radiation by multiple partial reflection on the surface of the film into at least the two bundles of electromagnetic radiation emanating from the thin film, the step of filtering includes utilizing a narrow band filter, and the steps of interfering and measuring includes imaging the filtered bundles with imaging optics on a detector, and the step of evaluating includes utilizing signal processing electronic circuitry for processing the measured intensities in accordance with the Airy formula so as to determine the thickness of the thin film in the planar direction thereof and the index of refraction thereof.

4. A processing according to claim 3, further comprising the step of heating the substrate.

5. A process according to claim 3, wherein the step of measuring includes utilizing a line detector for measuring a line-shaped region of the thin film.

6. A process according to claim 3, wherein the step of measuring includes utilizing a matrix detector for measuring the entire thin film.

7. A process according to claim 3, wherein the at least two bundles of electromagnetic radiation which are utilized for measurement emanate from the surface of the thin film in a direction substantially perpendicular to the surface of the thin film.

8. A process according to claim 3, wherein the step of measuring includes measuring the time characteristics of the intensities of the interfering bundles of electromagnetic radiation.

9. A process according to claim 3, wherein the thickness of the thin film and the index of refraction of the thin film are measured during an application process wherein the substrate is disposed in an application processing chamber and the electromagnetic radiation radiates outwardly of the application processing chamber for measurement.

10. A process according to claim 9, wherein the application processing effected in the application processing chamber is a removal process.

11. Apparatus for enabling spatially resolved measurement of a thickness of a thin film on a substrate, comprising the substrate forming thermal radiation as a means for emitting electromagnetic radiation and causing at least two bundles of electromagnetic radiation exhibiting a phase difference after passing through differing path lengths in the thin film to emanate from the thin film at different points in a planar direction of the thin film, means for filtering from the at least two bundles of electromagnetic radiation all frequency proportions other than an approximately monochromatic proportion out of a continuous spectrum of the thermal radiation, means for interfering the at least two filtered bundles of electromagnetic radiation, means for measuring the intensities of the interfering bundles of electromagnetic radiation, and means for evaluating the measured intensities so as to at least obtain the spatially resolved measurement of the thickness of the thin film on the substrate in the planar direction of the thin film.

12. An apparatus according to claim 11, wherein the means for evaluating includes means for obtaining the refractive index of the thin film.

13. An apparatus according to claim 12, wherein the thermal radiation emanates from an arbitrary point in the substrate, is refracted on an interface between the substrate and the thin film having the thickness thereof to be measured, and is separated by multiple partial refraction on the surface of the film into the at least two bundles of electromagnetic radiation emanating from the thin film, further comprising means for holding the substrate, the filtering means and the measuring means including a filter, imaging optics and a detector disposed along an optical axis, the evaluating means including signal-processing electronic circuit means for processing the measured intensities in accordance with the Airy formula so as to determine the thickness of the thin film in the planar direction thereof and the index of refraction thereof.

14. An apparatus according to claim 13, further comprising an application processing chamber having the substrate holder with the substrate and thin film thereon arranged therein, the application processing chamber including inlet valves and a window transparent to the electromagnetic radiation vacuum tightly disposed therein, the window being arranged in the optical axis.

15. An apparatus according to claim 14, wherein the optical axis extends substantially perpendicularly to a surface of the substrate.

16. An apparatus according to claim 13, wherein the measuring means includes a camera having semiconductor image converts arranged in a line pattern.

17. An apparatus according to claim 15, wherein the filtering means includes one of a grating monochromator and a prism monochromator.

18. An apparatus according to claim 13, wherein the measuring means includes a camera with a semiconductor image converter matrix.

19. An apparatus according to claim 18, wherein the filtering means includes a narrow-band interference filter.

20. An apparatus according to claim 13, wherein the substrate holder includes a heating element for heating the substrate.

21. An apparatus according to claim 14, wherein the application processing chamber is a furnace.

* * * * *